(12) United States Patent
Pribanic et al.

(10) Patent No.: US 8,459,524 B2
(45) Date of Patent: Jun. 11, 2013

(54) TISSUE FASTENING SYSTEM FOR A MEDICAL DEVICE

(75) Inventors: Russell Pribanic, New Milford, CT (US); Michael A. Zemlok, Prospect, CT (US); Stanislaw Marczyk, Stratford, CT (US); Adam J. Ross, Prospect, CT (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 12/813,604

(22) Filed: Jun. 11, 2010

(65) Prior Publication Data

US 2011/0036888 A1 Feb. 17, 2011

Related U.S. Application Data

(60) Provisional application No. 61/233,871, filed on Aug. 14, 2009.

(51) Int. Cl.
*A61B 17/04* (2006.01)
*A61B 17/10* (2006.01)

(52) U.S. Cl.
USPC .................................................. 227/179.1

(58) Field of Classification Search
USPC ................ 227/175.1–182.1; 606/300–315, 606/217–219, 75, 138
See application file for complete search history.

(56) References Cited

U.S. PATENT DOCUMENTS

| | | | |
|---|---|---|---|
| 1,982,207 A | 11/1934 | Furniss | |
| 2,033,039 A | 3/1936 | Limpert | |
| 2,391,792 A | 12/1945 | Miles et al. | |
| 2,832,129 A | 4/1958 | Forster | |
| 3,687,138 A | 8/1972 | Jarvik | |
| 4,204,541 A | 5/1980 | Kapitanov | |
| 4,679,572 A | 7/1987 | Baker, Jr. | |
| 4,930,674 A * | 6/1990 | Barak | 227/179.1 |
| 5,053,047 A | 10/1991 | Yoon | |
| 5,098,374 A | 3/1992 | Othel-Jacobsen et al. | |
| 5,163,343 A | 11/1992 | Gish | |
| 5,188,636 A * | 2/1993 | Fedotov | 606/144 |
| 5,309,927 A | 5/1994 | Welch | |
| 5,342,389 A | 8/1994 | Haber et al. | |
| 5,356,424 A | 10/1994 | Buzerak et al. | |
| 5,437,266 A | 8/1995 | McPherson et al. | |

(Continued)

FOREIGN PATENT DOCUMENTS

EP 1836971 A2 9/2007

OTHER PUBLICATIONS

European Search Report for corresponding EP 10 25 1444 application, date of completion is Dec. 9, 2010 (3 pages).

*Primary Examiner* — Robert Long

(57) ABSTRACT

A surgical fastening device includes a handle assembly having a stationary handle and a movable handle and an elongated member extending distally from the handle portion. The elongated member includes a distal end portion. The device also includes a pair of firing rods operably coupled with the movable handle and movable between a proximal position and a distal position. A tool assembly has a plurality of helical fasteners supported therein and includes a pair of opposing jaw members. At least one of the jaw members is movable in relation to the other jaw member between spaced and approximated positions. The jaw members are configured to form a pair of radial channels when the jaw members are in the approximated position. The firing rods are configured to advance helical fasteners through at least one radial channel and into tissue upon movement from the proximal position to the distal position.

18 Claims, 17 Drawing Sheets

U.S. PATENT DOCUMENTS

| | | |
|---|---|---|
| 5,456,145 A | 10/1995 | Cosenza |
| 5,545,148 A | 8/1996 | Wurster |
| 5,582,616 A | 12/1996 | Bolduc et al. |
| 5,662,683 A | 9/1997 | Kay |
| 5,762,069 A * | 6/1998 | Kelleher et al. ............... 600/564 |
| 5,782,844 A | 7/1998 | Yoon et al. |
| 5,810,851 A | 9/1998 | Yoon |
| 5,810,882 A | 9/1998 | Bolduc et al. |
| 5,824,008 A | 10/1998 | Bolduc et al. |
| 5,830,221 A * | 11/1998 | Stein et al. .................... 606/157 |
| 5,865,361 A | 2/1999 | Milliman et al. |
| 5,915,616 A | 6/1999 | Viola et al. |
| 5,964,394 A | 10/1999 | Robertson |
| 5,964,772 A | 10/1999 | Bolduc et al. |
| 5,972,001 A | 10/1999 | Yoon |
| 5,989,242 A | 11/1999 | Saadat et al. |
| 6,015,416 A | 1/2000 | Stefanchik et al. |
| 6,036,701 A | 3/2000 | Rosenman |
| 6,202,914 B1 | 3/2001 | Geiste et al. |
| 6,238,415 B1 | 5/2001 | Sepetka et al. |
| 6,258,119 B1 | 7/2001 | Hussein et al. |
| 6,296,656 B1 | 10/2001 | Bolduc et al. |
| 6,468,309 B1 | 10/2002 | Lieberman |
| 6,488,683 B2 | 12/2002 | Lieberman |
| 6,527,774 B2 | 3/2003 | Lieberman |
| 6,544,265 B2 | 4/2003 | Lieberman |
| 6,551,319 B2 | 4/2003 | Lieberman |
| 6,551,322 B1 | 4/2003 | Lieberman |
| 6,562,051 B1 | 5/2003 | Bolduc et al. |
| 6,663,633 B1 | 12/2003 | Pierson, III |
| 6,689,168 B2 | 2/2004 | Lieberman |
| 6,849,081 B2 | 2/2005 | Sepetka et al. |
| 6,884,248 B2 | 4/2005 | Bolduc et al. |
| 6,942,676 B2 | 9/2005 | Buelna |
| 6,953,462 B2 | 10/2005 | Lieberman |
| 6,960,217 B2 | 11/2005 | Bolduc |
| 6,984,241 B2 | 1/2006 | Lubbers et al. |
| 7,077,850 B2 | 7/2006 | Kortenbach |
| 7,229,452 B2 | 6/2007 | Kayan |
| 7,347,863 B2 | 3/2008 | Rothe et al. |
| 7,361,180 B2 | 4/2008 | Saadat et al. |
| 7,637,905 B2 * | 12/2009 | Saadat et al. ...................... 606/1 |
| 7,954,687 B2 * | 6/2011 | Zemlok et al. ............. 227/176.1 |
| 2001/0002438 A1 | 5/2001 | Sepetka et al. |
| 2003/0135226 A1 | 7/2003 | Bolduc et al. |
| 2003/0229350 A1 | 12/2003 | Kay |
| 2004/0049227 A1 | 3/2004 | Jervis |
| 2004/0073237 A1 | 4/2004 | Leinsing |
| 2004/0133214 A1 | 7/2004 | Kayan |
| 2004/0153101 A1 | 8/2004 | Bolduc et al. |
| 2004/0167545 A1 | 8/2004 | Sadler et al. |
| 2005/0154417 A1 | 7/2005 | Sepetka et al. |
| 2005/0171562 A1 | 8/2005 | Criscuolo et al. |
| 2005/0177180 A1 | 8/2005 | Kaganov et al. |
| 2005/0187613 A1 | 8/2005 | Bolduc et al. |
| 2005/0192474 A1 | 9/2005 | Vanden Hoek et al. |
| 2005/0256531 A9 | 11/2005 | Bolduc et al. |
| 2006/0020326 A9 | 1/2006 | Bolduc et al. |
| 2006/0030885 A1 | 2/2006 | Hyde |
| 2006/0036265 A1 | 2/2006 | Dant |
| 2006/0129154 A1 | 6/2006 | Shipp |
| 2006/0142787 A1 | 6/2006 | Weller et al. |
| 2006/0212047 A1 | 9/2006 | Abbott et al. |
| 2006/0212048 A1 | 9/2006 | Crainich |
| 2006/0212071 A1 | 9/2006 | Ginn et al. |
| 2007/0021756 A1 | 1/2007 | Kortenbach |
| 2007/0073315 A1 | 3/2007 | Ginn et al. |
| 2007/0142849 A1 | 6/2007 | Ewers et al. |
| 2007/0208358 A1 | 9/2007 | Kayan |
| 2007/0225737 A1 * | 9/2007 | Messerly et al. ............. 606/151 |
| 2007/0282356 A1 * | 12/2007 | Sonnenschein et al. ...... 606/153 |
| 2007/0299470 A1 | 12/2007 | Vanden Hoek et al. |
| 2008/0004640 A1 | 1/2008 | Ellingwood |
| 2008/0039879 A1 | 2/2008 | Chin et al. |
| 2008/0086154 A1 | 4/2008 | Taylor et al. |
| 2008/0097523 A1 | 4/2008 | Bolduc et al. |
| 2009/0005808 A1 * | 1/2009 | Hess et al. ................ 606/219 |
| 2009/0114701 A1 * | 5/2009 | Zemlok et al. ............. 227/176.1 |
| 2009/0209946 A1 * | 8/2009 | Swayze et al. .................... 606/1 |

* cited by examiner

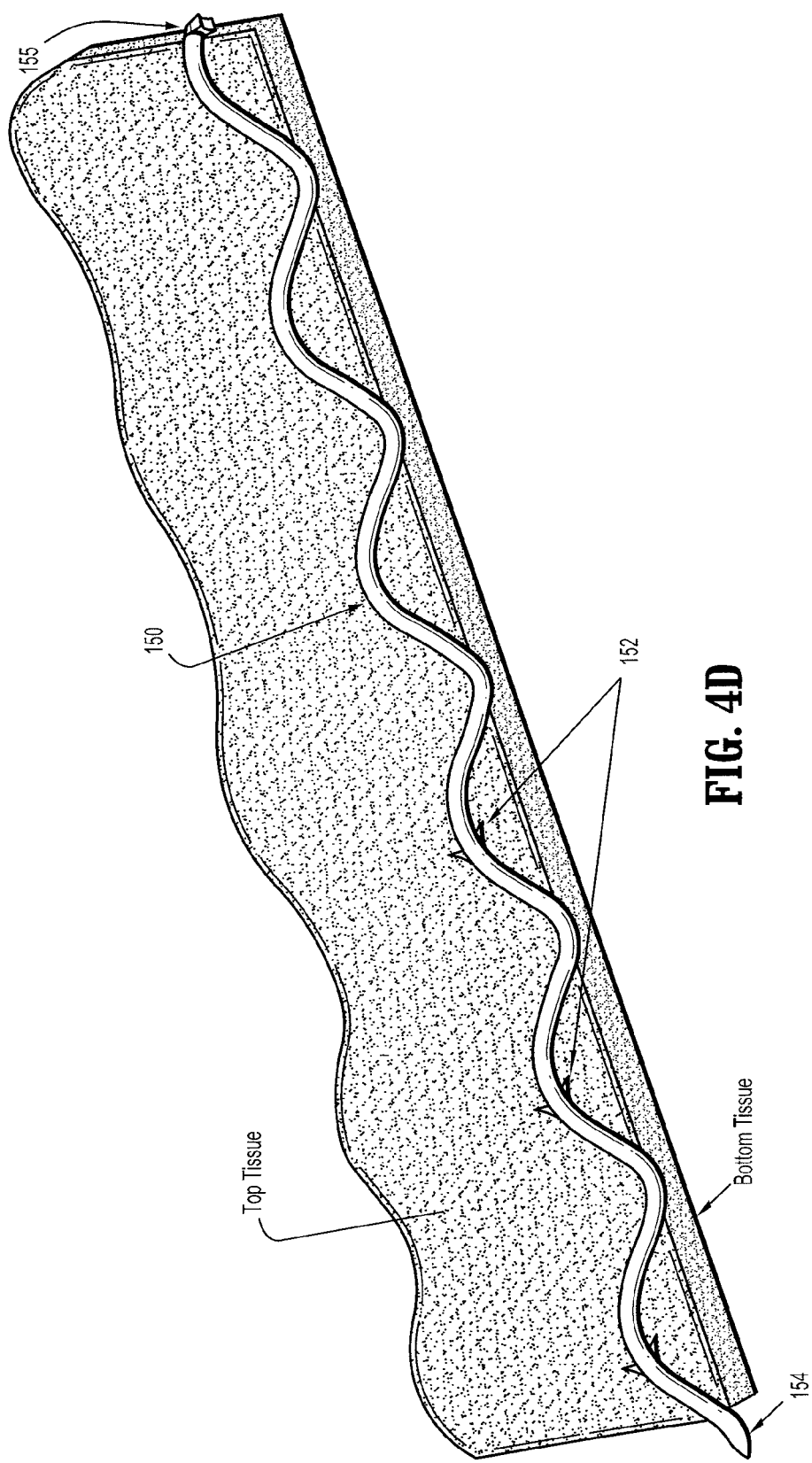

TISSUE FASTENING SYSTEM FOR A MEDICAL DEVICE

CROSS REFERENCE TO RELATED APPLICATION

The present application claims the benefit of and priority to U.S. Provisional Application Ser. No. 61/233,871 filed on Aug. 14, 2009, the entire contents of which are incorporated herein by reference.

BACKGROUND

1. Technical Field

The present disclosure relates to a surgical fastener applying device and, more particularly, to a surgical fastener applying device adapted to apply helical fasteners to tissue.

2. Background of Related Art

Commercially available surgical fastening apparatus are well known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. U.S. Pat. Nos. 5,915,616; 6,202,914; 5,865,361; and 5,964,394 each describe one or more suitable apparatus which may be employed while performing one of these procedures.

In general, a surgical fastening apparatus will include an anvil that is approximated relative to a fastener cartridge during use. The anvil includes depressions that are aligned with, and/or are in registration with slots defined in the cartridge, through which the fasteners will emerge, to effectuate formation. The fastener cartridge typically has one or more rows of fasteners disposed laterally or radially of a channel that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

During each of the aforementioned surgical procedures, the tissue is initially gripped or clamped such that individual fasteners can be ejected from the cartridge, through the slots, and forced through the clamped tissue. Thereafter, the fasteners are formed by driving them into the depressions formed on the anvil.

Conventional surgical fastening apparatus generally require removal of the device from the surgical site to reload fasteners, thereby wasting valuable operating time. Exacerbating this problem is the generally cumbersome nature of conventional apparatus, which makes navigating the instrument in, out, and around the surgical site difficult. Accordingly, the joining of tissue utilizing such instruments may cause longer than necessary operating time.

Consequently, it would be advantageous to provide a surgical fastening apparatus wherein removal of the device from the surgical site may be reduced or eliminated, thereby reducing operating time. It would further be advantageous to provide a surgical fastening apparatus with reduced size (e.g., girth, length, width, etc.) to improve maneuverability in and around the surgical site.

SUMMARY

According to an embodiment of the present disclosure, a surgical fastening device includes a handle assembly having a stationary handle and a movable handle and an elongated member extending distally from the handle portion. The elongated member includes a distal end portion. The device also includes a pair of firing rods operably coupled with the movable handle and movable between a proximal position and a distal position. A tool assembly has a plurality of helical fasteners supported therein and includes a pair of opposing jaw members. At least one of the jaw members is movable in relation to the other jaw member between spaced and approximated positions. The jaw members are configured to form a pair of radial channels when the jaw members are in the approximated position. The firing rods are configured to advance helical fasteners through at least one radial channel and into tissue upon movement from the proximal position to the distal position.

BRIEF DESCRIPTION OF THE DRAWINGS

Embodiments of the presently disclosed tissue fastening device are disclosed herein with reference to the drawings wherein:

FIG. 4D is an enlarged perspective view of a load coil mechanically joining tissue;

DETAILED DESCRIPTION

Figure 1:
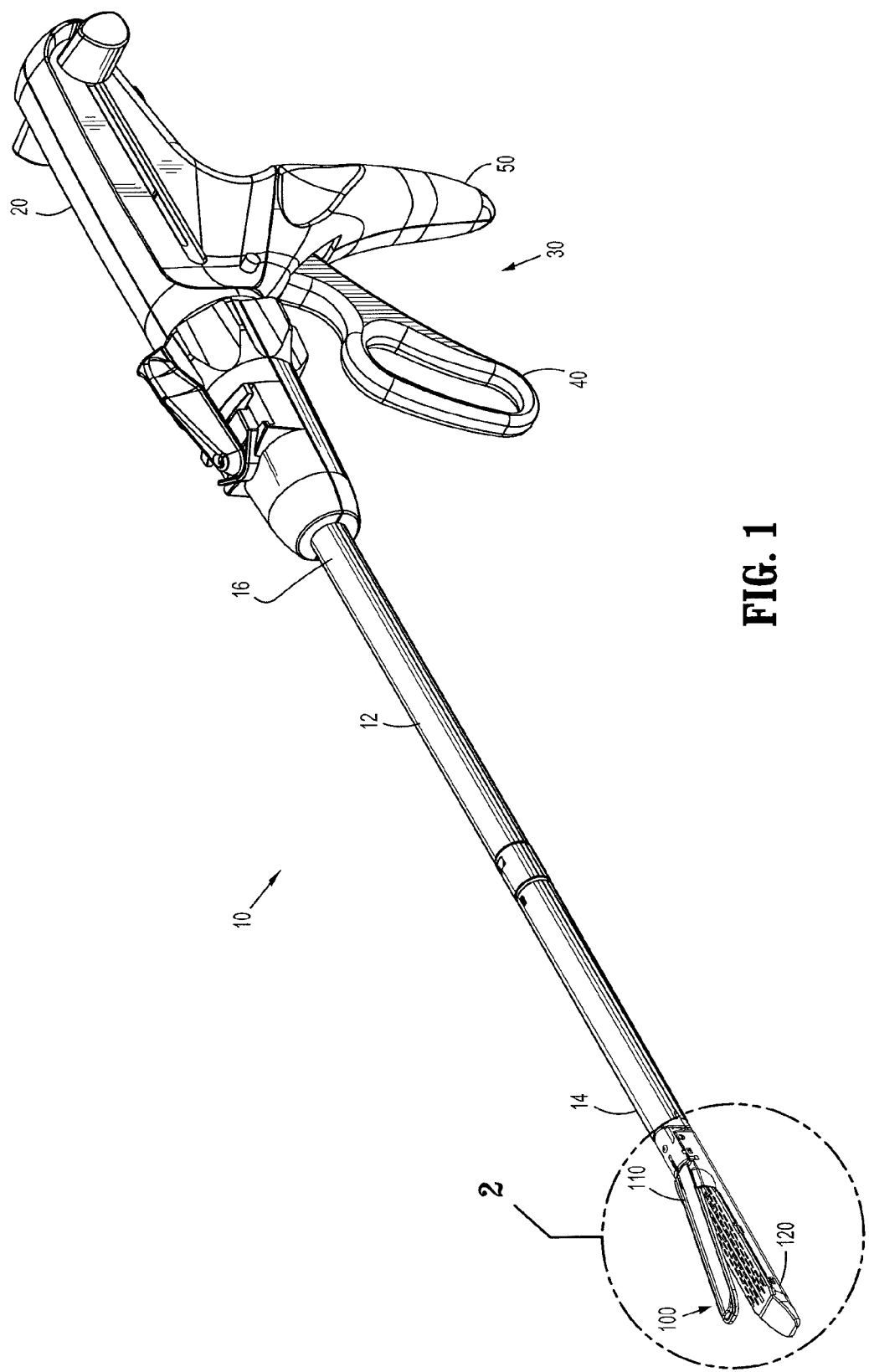
FIG. 1 is a schematic view of a surgical fastening device in accordance with an embodiment of the present disclosure.

Embodiments of the presently disclosed surgical fastening device will now be described in detail with reference to the drawings in which like reference numerals designate identical or corresponding element in each of the several views.

With reference to FIG. 1, an embodiment of a surgically fastener applying device 10 is shown for use with various surgical procedures and generally includes a housing 20, a handle assembly 30, and an operative tool assembly 100. Device 10 includes a shaft 12 that has a distal end 14 dimensioned to mechanically engage the tool assembly 100 and a proximal end 16 that mechanically engages the housing 20. In the drawings and in the descriptions that follow, the term "proximal", as is traditional, will refer to the end of the device 10 that is closer to the user, while the term "distal" will refer to the end that is further from the user.

Handle assembly 30 includes a fixed handle 50 and a movable handle 40. Fixed handle 50 is integrally associated with housing 20 and handle 40 is movable relative to fixed handle 50 as explained in more detail below with respect to the operation of the device 10.

For a more detailed discussion of the approximation and firing of surgical fastener applying device 10, reference is made to commonly owned U.S. Pat. No. 5,865,361, currently assigned to Tyco Healthcare Group LP, the entire contents of which is incorporated herein by reference. Movable handle 40 of handle assembly 30 is operatively connected to a drive assembly (not explicitly shown) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. With this purpose in mind, the drive assembly may include any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components to effect the intended operation of device 10. Subsequently, continued movement of movable handle 40 imparts a driving force to a pair of firing rods 134a, 134b (either independently or dependently) causing the rods 134a, 134b to advance linearly in a distal direction. The jaw members 110, 120 are moved closer relative to each other and a force is transmitted to a coil cartridge 148 disposed within device 10 to thereby eject one or more load coils 150 into tissue clamped between jaw members 110, 120, as will be discussed in further detail below.

Figure 2:
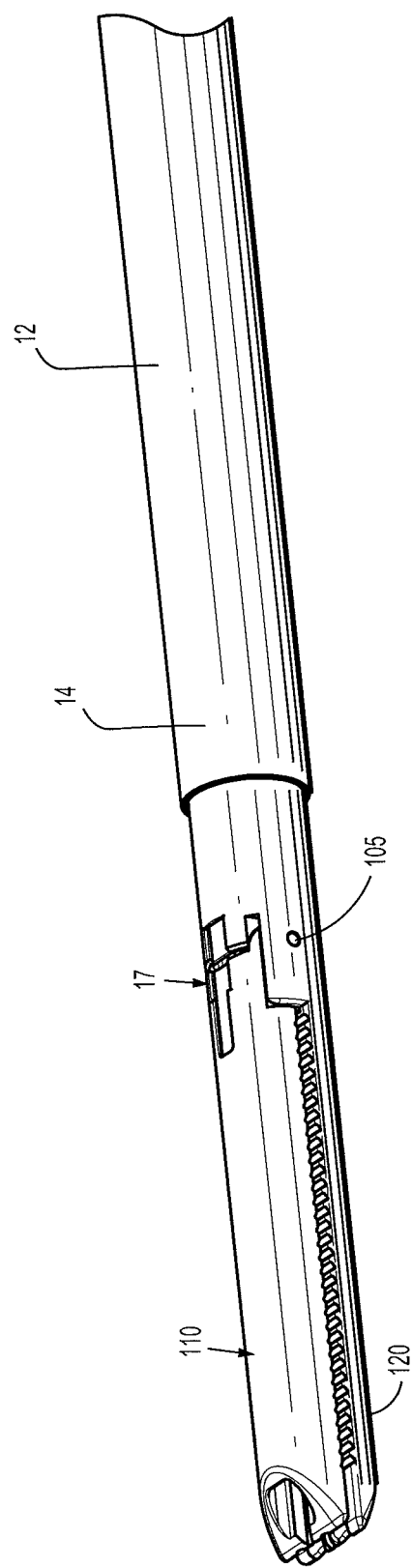
FIG. 2 is an enlarged view of the indicated area of detail shown in FIG. 1.

In embodiments, the tool assembly 100 may be designed as a unilateral assembly, as shown in FIGS. 1 and 2, i.e., jaw member 120 is fixed relative to the shaft 12 and jaw member 110 pivots about a pivot pin 105 (see FIG. 2) relative to jaw member 120 to grasp tissue, or as a bilateral assembly (not shown), i.e., jaw members 110 and 120 pivot about pivot pin 105 relative to each other to grasp tissue.

Figure 4A:
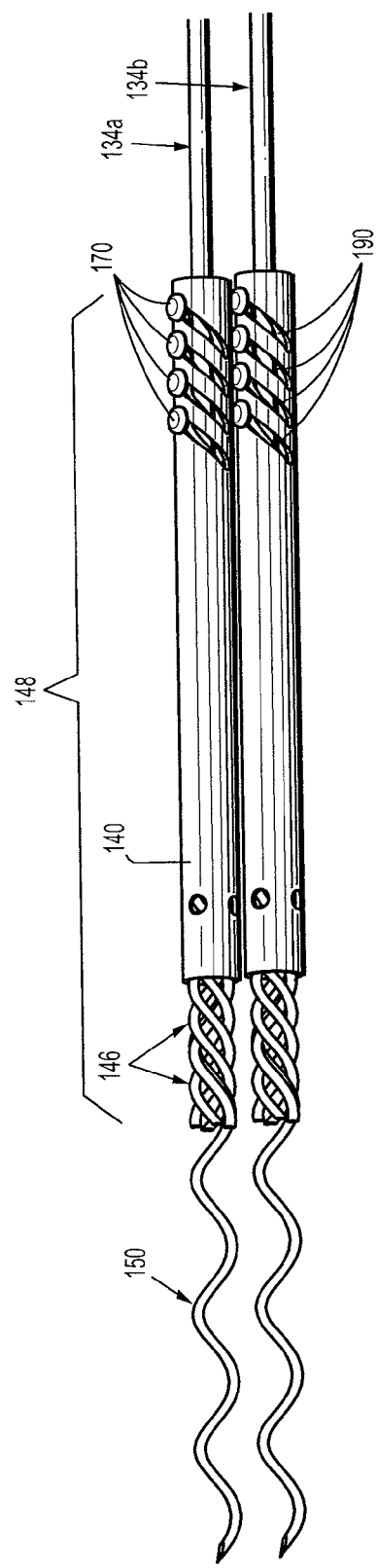
FIG. 4A is a perspective view of a coil cartridge in accordance with an embodiment of the present disclosure.
Figure 4B:
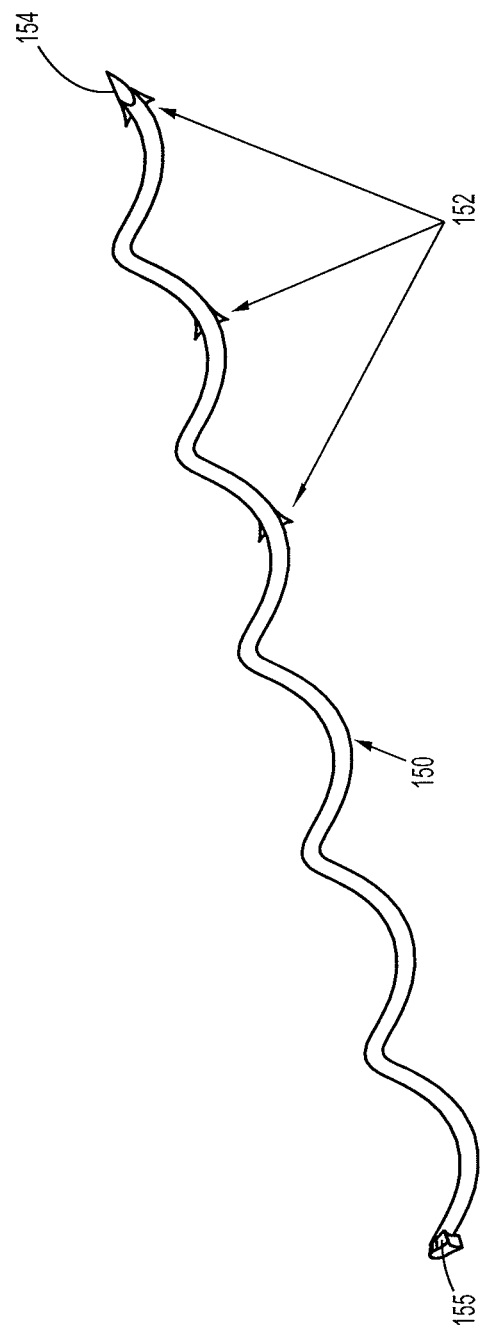
FIG. 4B is a perspective view of a load coil of the coil cartridge of FIG. 4A.

With reference to FIG. 2, the tool assembly 100 includes one stationary or fixed jaw member 120 mounted in fixed relation to the shaft 12 and a pivoting jaw member 110 mounted about a pivot pin 105 attached to the stationary jaw member 120. The distal end 14 of shaft 12 includes a leaf spring 17 configured to engage a proximal end of jaw member 110 to bias jaw member 110 in spaced relation to jaw member 120, as will be discussed in further detail below. In some embodiments, fixed jaw member 120 may be monolithically formed with shaft 12, e.g., stationary jaw member 120 may be defined by the distal end 14 of shaft 12. As discussed in further detail below, tool assembly 100 is configured to apply helical wire segments or load coils into two adjacent tissues, thereby mechanically joining them (see FIG. 4D).

Movable handle 40 of handle assembly 30 is operatively connected to a drive assembly (not explicitly shown) that, together, mechanically cooperate to impart linear movement of a pair of firing rods 134a, 134b between a proximal position (i.e., a "loaded position") and a distal position (e.g., a "firing position"). Firing rods 134a and 134b may move independent or dependent relative to one another.

Figure 3A:
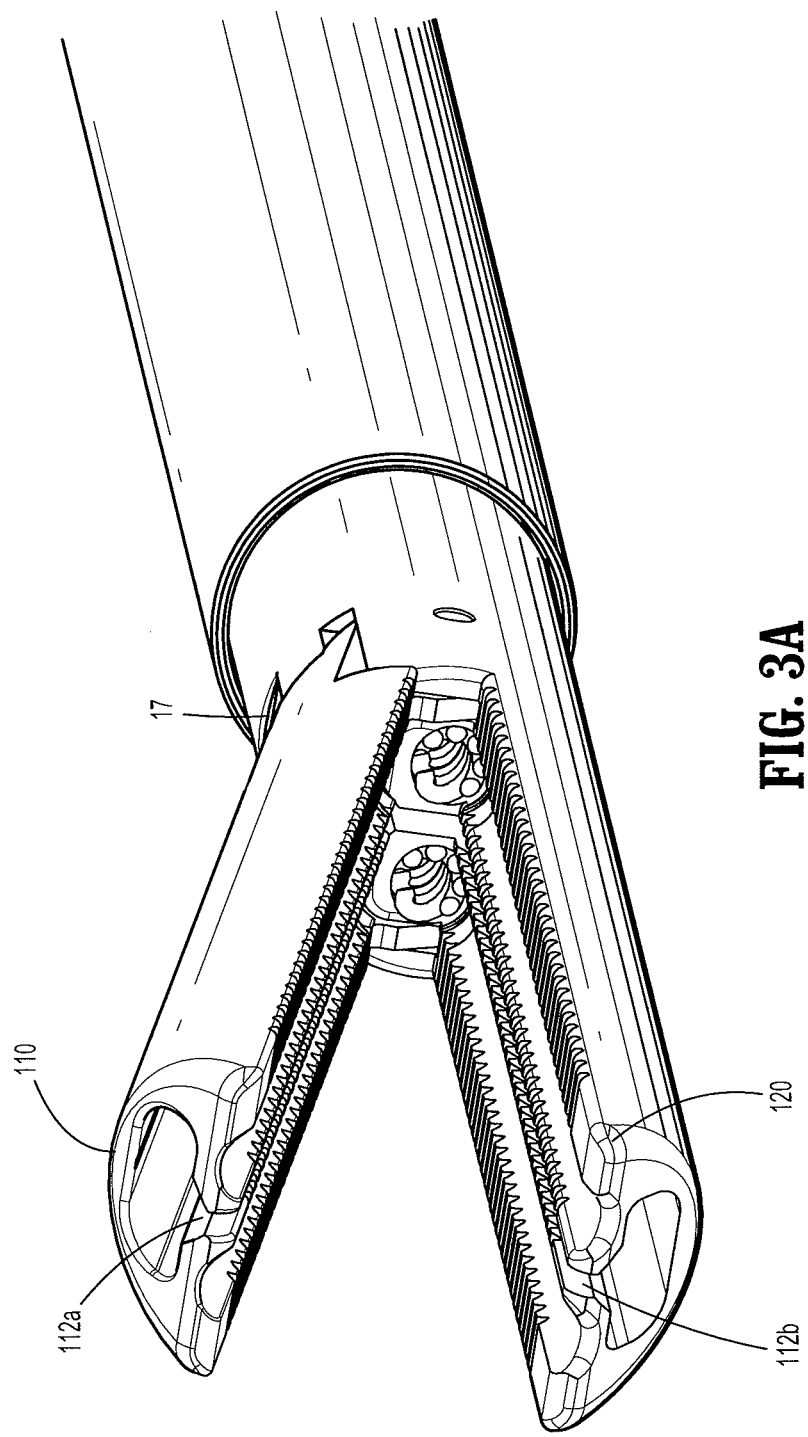
FIG. 3A is an enlarged perspective view of a distal end of the surgical fastening device of FIG. 1.
Figure 3B:
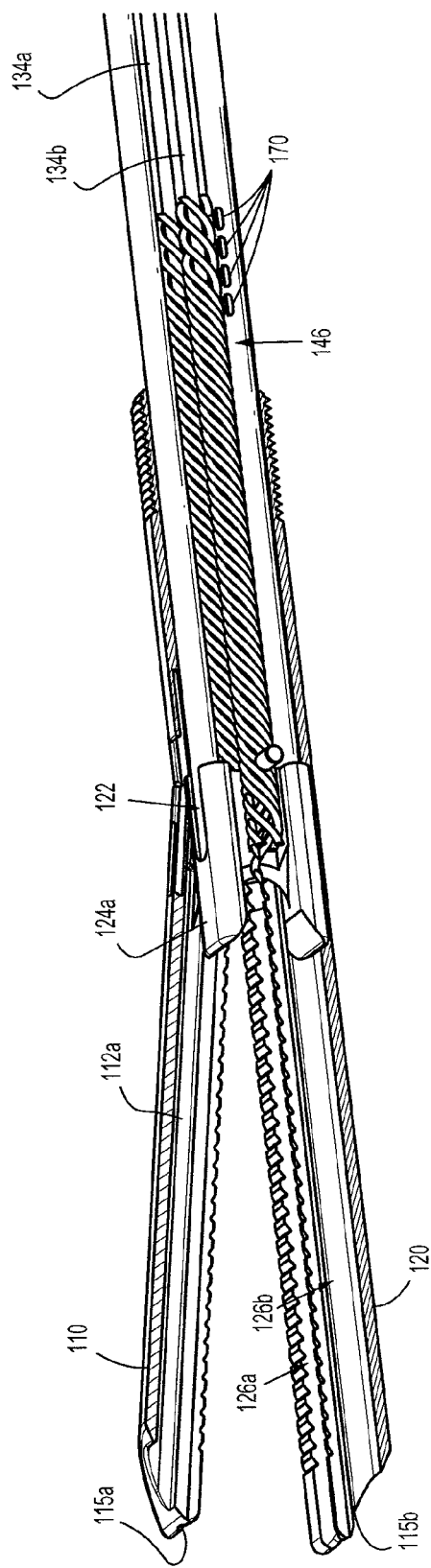
FIG. 3B is a partial cross-section view of a distal end of the surgical fastening device of FIG. 1.

With reference to FIGS. 3A and 3B, an inner surface of each of jaw members 110, 120 includes a channel or knife slot 115a, 115b, respectively, that is configured to accommodate longitudinal movement of a cutting element 122, such that fastened tissue may be severed along a cut-line. More specifically, the cutting element 122 advances through knife channels 115a, 115b when activated to progressively and selectively divide tissue along an ideal tissue plane in a precise manner to effectively and reliably divide the tissue. In embodiments, the device 10 may be configured such that cutting element 122 may only be advanced through knife channels 115a, 115b to cut tissue when jaw members 110, 120 are in the clamping or closed position, thus, preventing accidental or premature activation of the cutting element 122 through tissue.

In the illustrated embodiment of FIG. 3B, cutting element 122 is I-beam shaped and includes a pair of opposing ramp lead-ins that are substantially identical with only one lead-in 124a shown. Lead-ins are configured to engage a respective mating slot 112a, 112b axially disposed through jaw members 110, 120, respectively. When lead-ins of cutting element 122 are properly mated within mating slots 112a, 112b, respectively, jaw members 110, 120 may be biased to the closed position upon distal movement of cutting element 122. Once jaw members 110, 120 are in the closed position, a spring loaded pawl mechanism (not shown) interacting with a notch in the cutting element 122 prevents blade exposure and/or tissue cutting by preventing further distal movement of cutting element 122. When the pawl is disengaged from the notch (e.g., intentionally by the user), the cutting element 122 is permitted to progress distally to cut or transect tissue as desired.

The above-described clamping and cut method utilizing the cutting element 122 creates a consistent tissue clamping distance or thickness throughout a proximal-to-distal cutting element 122 translation. Although not explicitly illustrated, cutting element 122 may be formed from multiple flexible sheet metal blades that elastically deflect to allow angular translation about a pivot hinge.

As best shown in FIG. 3A, each of jaw members 110 and 120 includes a pair of semi-circular channels 116a, 116b and 126a, 126b respectively, axially disposed through an inner face thereof, and on opposing sides of knife channels 115a, 115b. Channel pairs 116a, 116b and 126a, 126b may be cut, coined, molded, formed, or machined into each jaw inner face. When jaws 110, 120 are in the closed position, channels 116a, 116b mirror or substantially align with channels 126a, 126b and vice-versa, thereby creating a pair of radial channels having circular cross-section, disposed on opposing sides of the centrally disposed knife channels 115a, 115b such that tissue may be joined along each edge of the cut line produced by cutting element 122.

With continuing reference to FIG. 3A, jaw member 110 may be urged open by leaf spring 17. More specifically, upon approximation of jaw members 110, 120 to the open position, leaf spring 17 operates to hold jaw member 110 is spaced relation to jaw member 120 until approximation of movable handle 40 to close jaw members 110, 120. In other embodiments, jaw member 110 may be leveraged open by cams, coil springs, torsion springs, and/or cables. Shaft 12 may be configured as a so-called "overtube" configured to be axially translated to slide over and close jaw members 110, 120.

Once jaw members 110 and 120 are in the closed position, one or more load coils 150 may be ejected from the tool assembly 100 via a pair of firing rods 134a, 134b. Movable handle 40 of handle assembly 30 is operatively connected to firing rods 134a, 134b such that approximation of movable handle 40 imparts linear movement of the firing rods 134a, 134b from a proximal position to a distal position. Generally, firing rods 134a, 134b substantially align with coil cartridges 148 disposed within the device 10. When jaw members 110, 120 are in the closed position, the circular cross-section of radial channels operate to captivate and guide load coils 150 into tissue clamped between jaw members 110, 120 upon distal advancement of firing rods 134a, 134b. In embodiments, each displacement cycle of firing rods 134a, 134b ejects a single load coil 150 from each coil cartridge 148. It may be most beneficial to fire load coils 150 substantially coincidentally with translation of cutting element 122 such that cutting element 122 travels immediately behind load coils 150 so that tissue is cut subsequent to fastening thereof. Cutting element 122 may also be deployed separately to transect clamped tissue after load coils 150 have been completely deployed from the coil cartridges 148.

With reference FIGS. 3B-5E, coil cartridges 148 include stationary coils 146 that are fixated to a rigid outer tube 140. Stationary coils 146 alternate with the load coils 150 and may include substantially similar pitch and diameter. Each load coil 150 is therefore isolated mechanically by adjacent stationary coils 146 and may be deployed without moving or influencing the other load coils 150 within the same coil cartridge 148. The rigid outer tube 140 covers the external diametrical shape of the load coils 150 in each coil cartridge 148. Fixation of stationary coils 146 may be achieved by any suitable fixation method, including without limitation, welding, brazing, and/or adhesives.

In other embodiments, the stationary coils 146 and rigid outer tube 140 combination may be supplemented with a tube that incorporates a similar internal helix ribbing or grooved pattern geometry to mechanically isolate each load coil 150. To obtain the desired geometry of the internal helix ribbing, any suitable method (e.g., machining, forming, molding, die-casting, EDM, broaching, etc.) may be used. In another embodiment of the rigid outer tube 140, load coils 150 are stacked end to end within rigid outer tube 140 and parallel to the longitudinal axis of the jaws 110, 120.

Figure 4C:
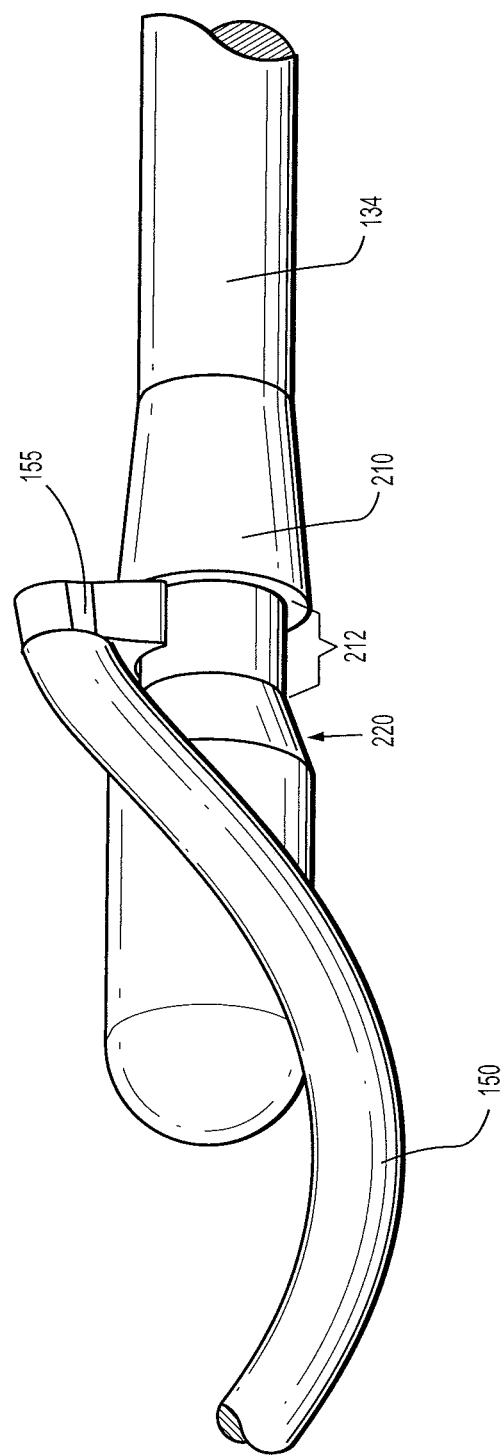
FIG. 4C is an enlarged perspective view of a load coil being engaged by the distal end of a firing rod in accordance with an embodiment of the present disclosure.
Figure 5A:
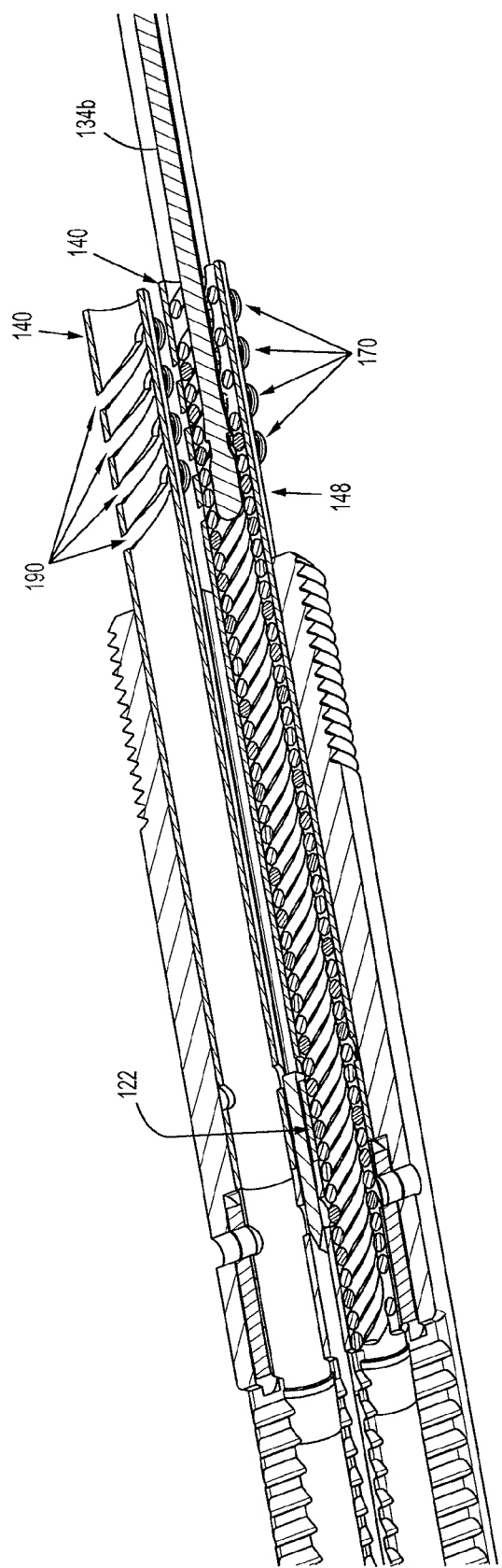
FIG. 5A is a cross-section view of the coil cartridge illustrating the outer-tube with coils removed.
Figure 5B:
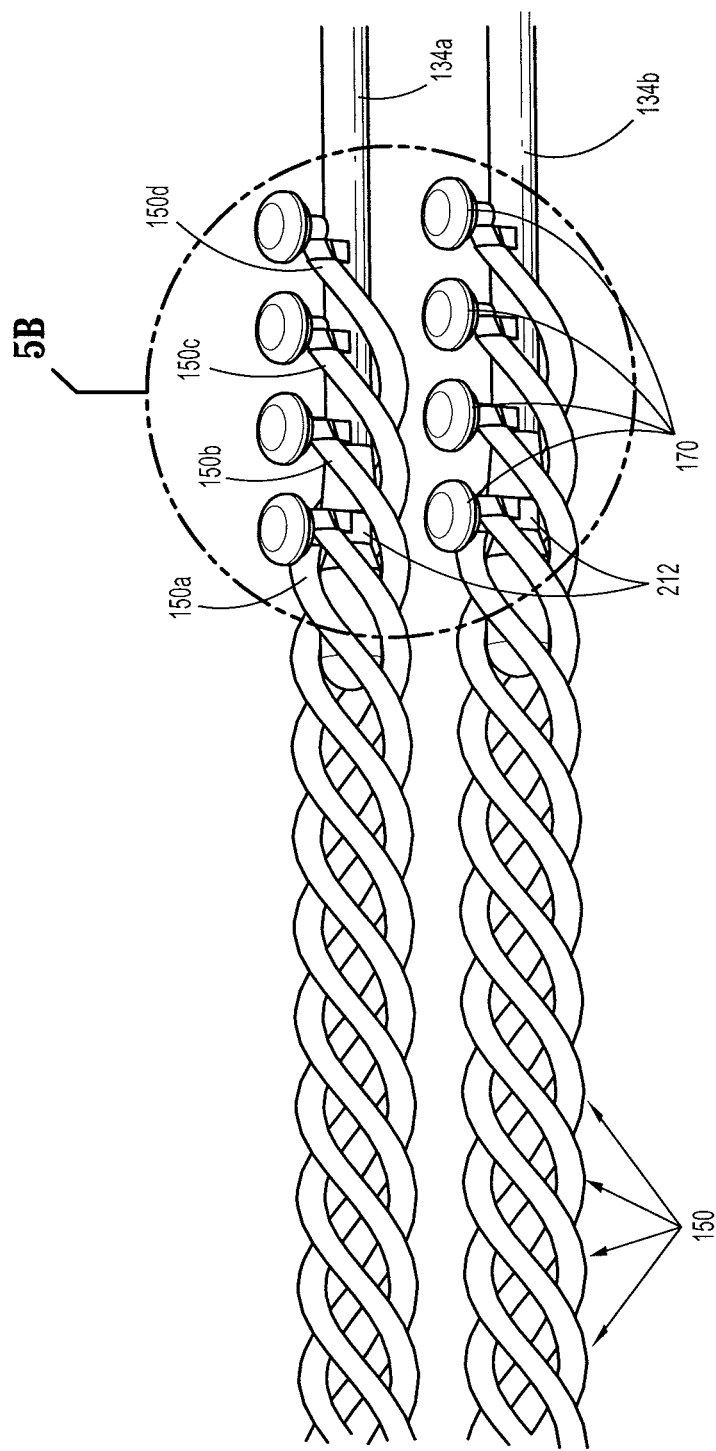
FIG. 5B is a perspective view of load coils engaged by the distal end of firing rods.
Figure 5C:
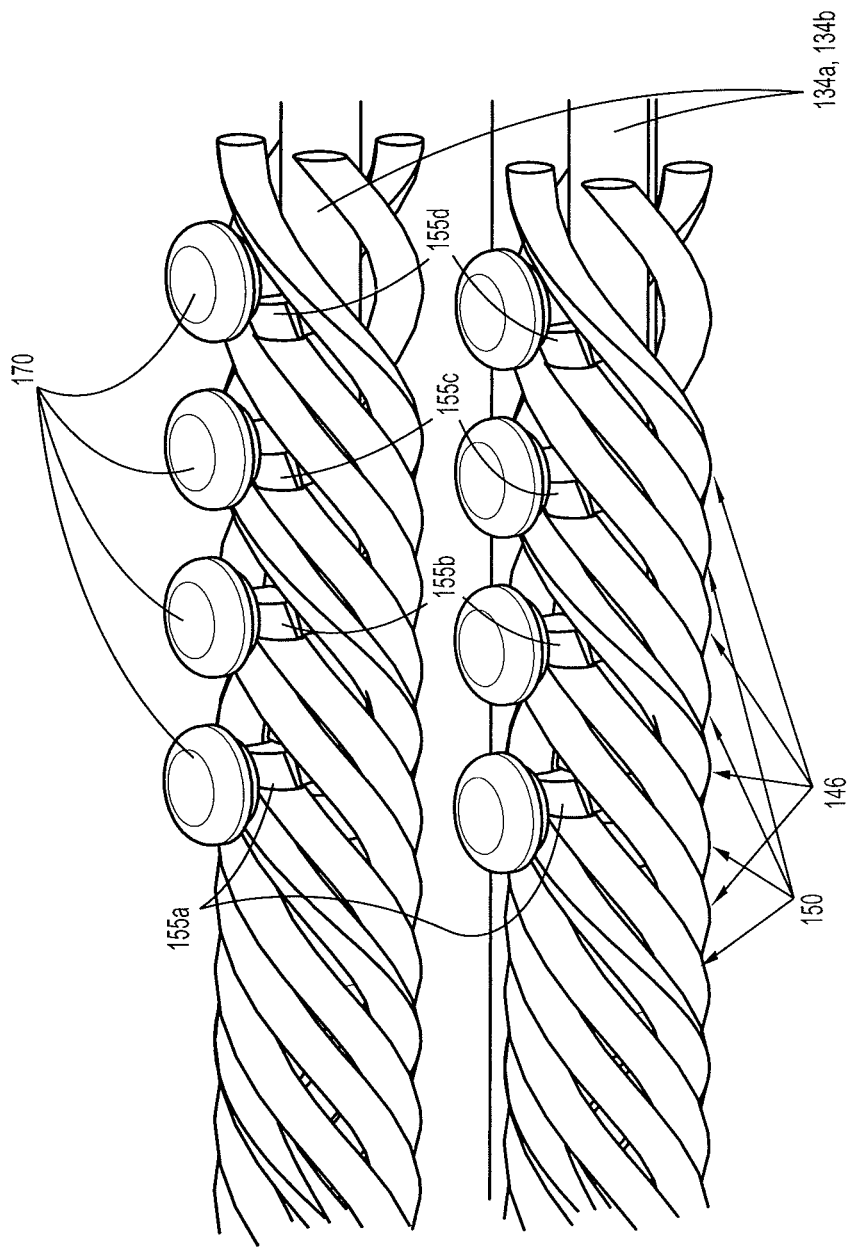
FIG. 5C is an enlarged view of the indicated area of detail shown in FIG. 5B.
Figure 5D:
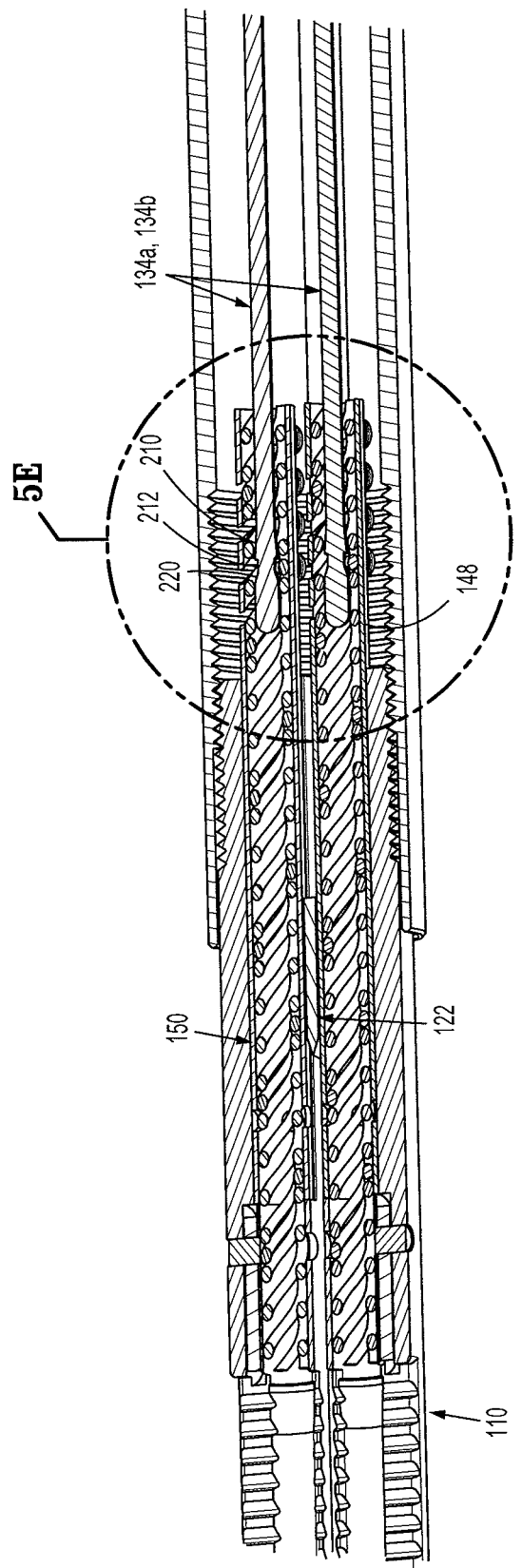
FIG. 5D is a cross-section view of the coil cartridge illustrating the stationary coils.
Figure 5E:
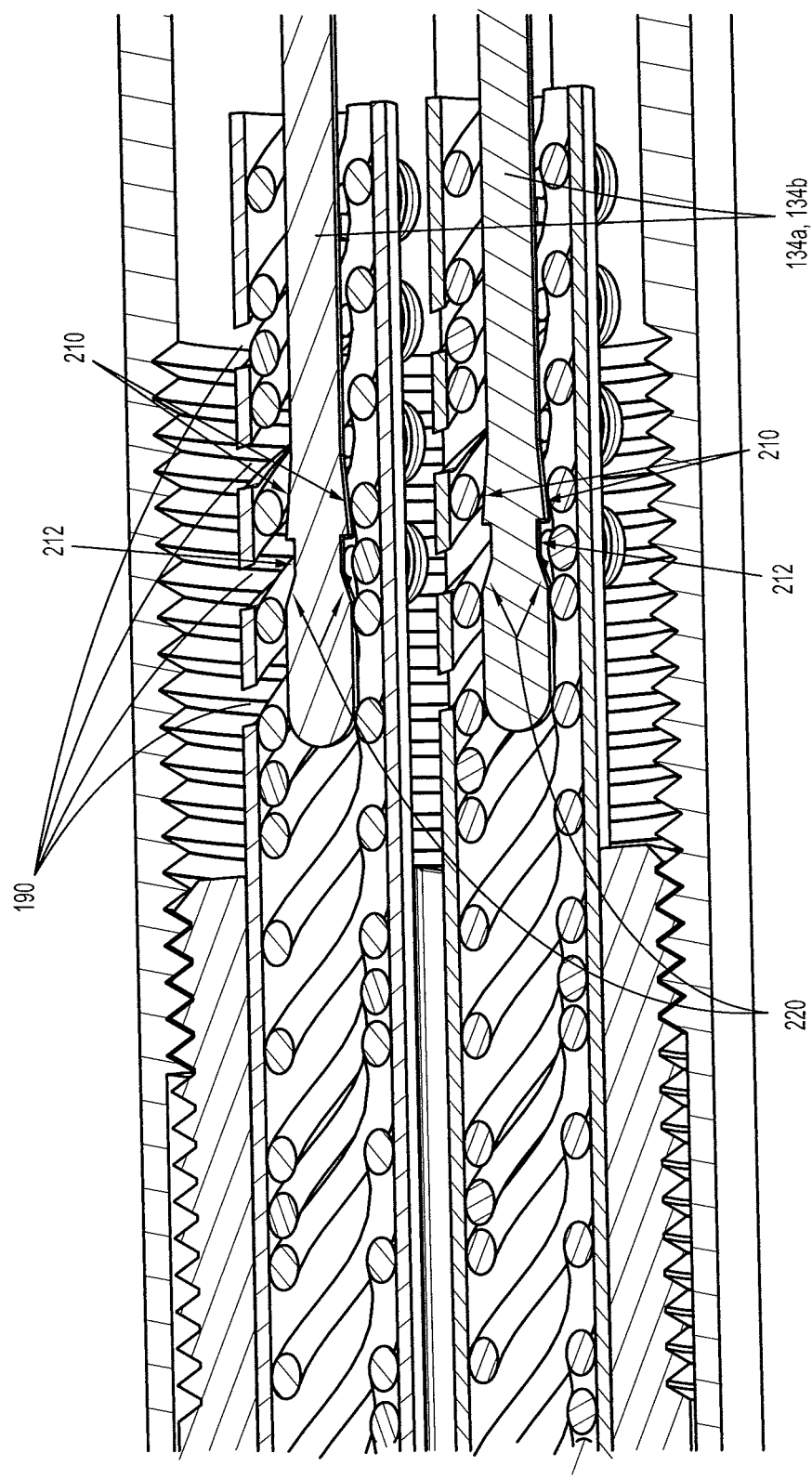
FIG. 5E is a cross-section view of the indicated area of detail shown in FIG. 5D.

With reference to FIGS. 4A-4D, each load coil 150 defines a protruding tab feature 155 at a proximal end thereof and a piercing tip 154 at a distal end thereof. Load coils 150 are staggered along the axis of the coil cartridge 148 such that each tab 155 is separated by a stop member 170 disposed in axial alignment therewith. The distal end of firing rods 134a, 134b are configured to engage the tab 155 of each load coil 150 one after the other such that, upon firing the device 10, firing rods 134a, 134b advance linearly in a distal direction to push a load coil 150 out of coil cartridge 148 and subsequently engage the tab 155 of the next load coil 150. More specifically and as best shown in FIG. 4C, upon firing, the tab 155 of each load coil 150 slides over a chamfer 210 defined on the distal end of firing rods 134a, 134b to displace the deflection incurred by the load coil 150 through a plurality of slots 190 (see FIG. 5A) defined through outer tube 140 of the coil cartridge 148. Upon sliding over the chamfer 210, tab 155 engages and aligns with a notch 212 formed in the distal end of firing rods 134a, 134b. In use, notch 212 of firing rods 134a, 134b initially engages the tab 155 on the proximal end of the lead or distal-most load coil 150 of each coil cartridge 148. While jaws 110 and 120 are clamped in the closed position, firing rods 134a, 134b are approximated linearly in a distal direction (e.g., via actuation of movable handle 40) such that the distal-most load coil 150 is advanced distally through one of the pair of radial channels formed through clamped jaws 110, 120. Upon distal movement of the load coil 150, the tab 155 on this load coil 150 rotates (clock-wise or counter clock-wise) about notch 212 of firing rods 134a, 134b, such that the load coil 150 screws into tissue clamped between jaw members 110, 120.

Once the firing rods 134a, 134b are fully translated distally, the load coil 150 is fully deployed into tissue. Firing rods 134a, 134b engage a stop member (not shown) within the distal end of the shaft 12. Upon retraction of firing rods 134a, 134b, a distal chamfer 220 defined by the distal end of firing rods 134a, 134b allows tab 155 on the load coil 150 to displace radially outward relative to firing rods 134a, 134b thereby releasing load coil 150 from notch 212. In embodiments, a spring loaded ratchet return (not shown) may be implemented into firing rods 134a, 134b and/or cutting element 122 to allow expedient or single-action retraction thereof. Firing rods 134a, 134b retract until the tab 155 of the next or now distal-most load coil 150 is engaged within notch 212 of firing rods 134a, 134b. Again, mechanical stops 170 limit proximal movement of firing rods 134a, 134b to this new home position such that the device 10 is ready to fire the next load coil 150 without removing the instrument and/or the end effector from the access port, trocar, orifice, or surgical site. In this manner, multiple load coils 150 may be fired during any one clamped tissue sequence. This may be advantageous during above-normal tissue pressures or tensions or when the tissue is extremely delicate and may require additional mechanical strength or support. In embodiments, two or more load coil tabs 155 may be aligned relative to the longitudinal axis of jaws 110, 120, thereby allowing two or more aligned load coils 150 to fire substantially simultaneously into clamped tissue.

The geometry of the tab 155 defined at the proximal end of each load coil 150 improves positioning of the load coil 150 by limiting the depth of advancement into tissue. In embodiments, one or more barbs 152 (see FIGS. 4B and 4D) may be disposed on the load coils 150 to captivate and/or anchor load coil 150 to tissue and/or to prevent unwanted migration of load coil 150 once implemented into tissue. Bio-absorbable materials may be coated at least partially on the load coil 150 to alleviate undesirable protrusions, bumps, sharps, or the like, within the patient's body. Further, load coils 150 may be produced with a layered hybrid wire that incorporates a thinner metal core wire and a bio-absorbable coating to create points, functional features and/or provide additional rigidity and strength. Once the coating absorbs into tissue, the wire is more flexible within tissue to prevent patient discomfort from rigid edges. Coatings may also incorporate, without limitation, polymers, paraffin, PTFE, and the like, to reduce frictional loads. Further, coatings may include antibiotics, coagulants, and/or pain reducing medications.

The firing rods 134a, 134b and cutting element 122 may be axially translated utilizing any suitable mechanism including, without limitation, a rack and pawl combination, a rack and pinion combination, a threaded lead screw, and/or a pulley and cable combination. Any of the above listed mechanisms may be operably coupled with any suitable source of power such as, without limitation, a manually operated pump, a manually operated crank, manually operated lever(s), an AC or DC powered electrical motor, springs, pneumatics, or hydraulics.

Figure 6A:
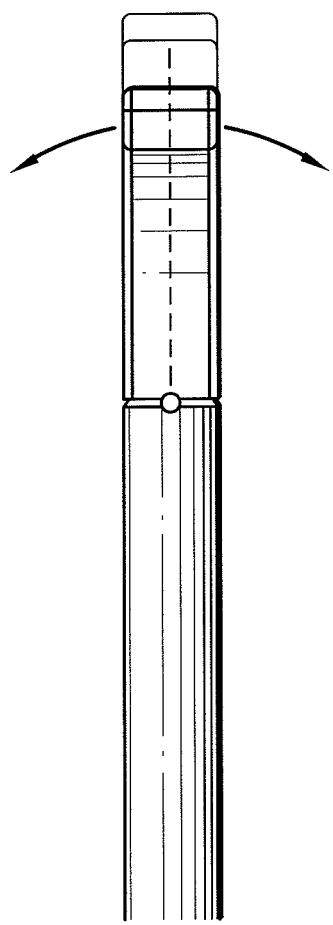
FIG. 6A is a top view of a tool assembly in accordance with an embodiment of the present disclosure.
Figure 6B:
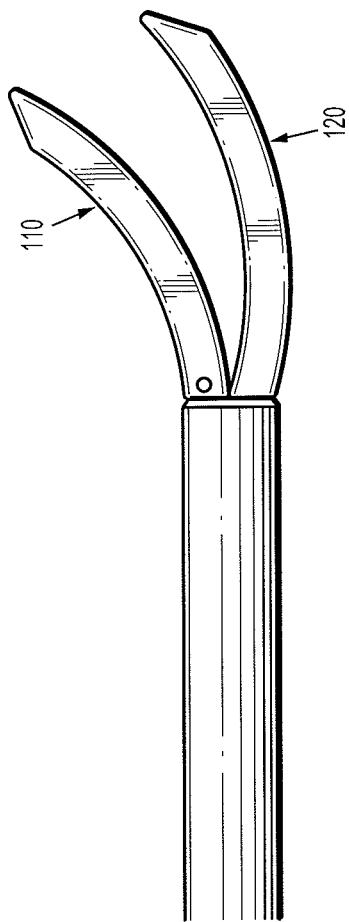
FIG. 6B is a side view of the tool assembly of FIG. 6A.
Figure 7A:
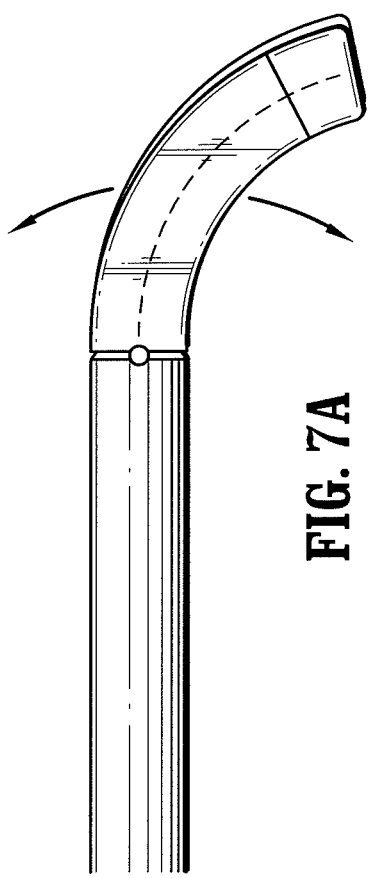
FIG. 7A is a top view of a tool assembly according to another embodiment of the present disclosure.
Figure 7B:
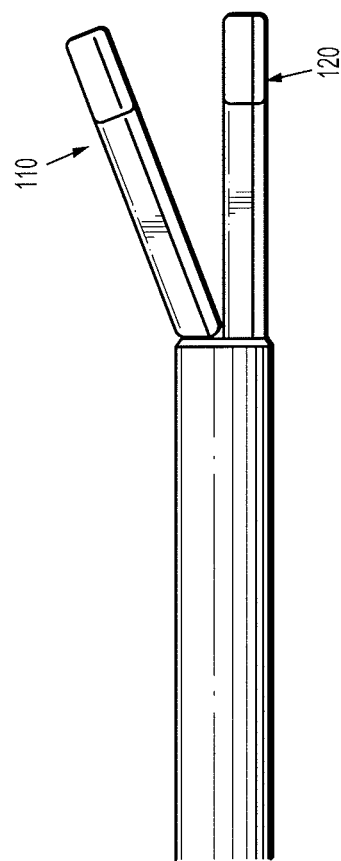
FIG. 7B is a side view of the tool assembly of FIG. 7A.

The firing rods 134a, 134b and/or cutting element 122 may be rigid or flexible to allow articulation around a joint or curvature. Because the load coils 150 may spiral through a range of bend radii, curvatures and shapes with the required circular cross section of the channels 116, 126 within jaw members 110, 120, the jaw members 110, 120 may be shaped to curve or bend in any direction relative to the longitudinal axis of the device 10 including upward along the central plane (see FIGS. 6A and 6B) or sideways (see FIGS. 7A and 7B).

Figure 8A:
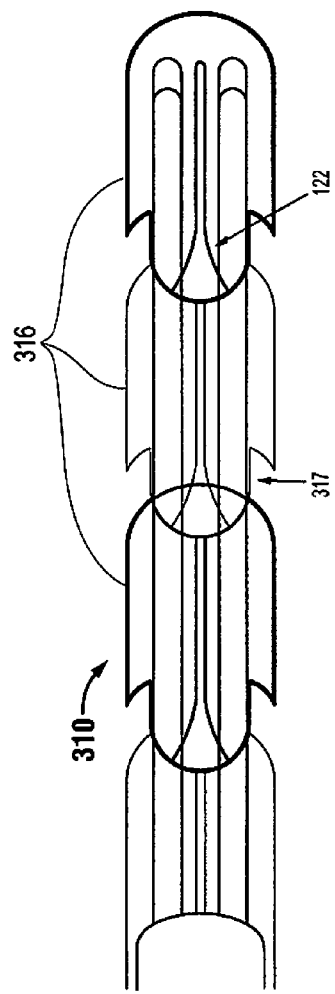
FIG. 8A is a top view of an inner surface of a tool assembly illustrating an unformed jaw member according to another embodiment of the present disclosure.
Figure 8B:
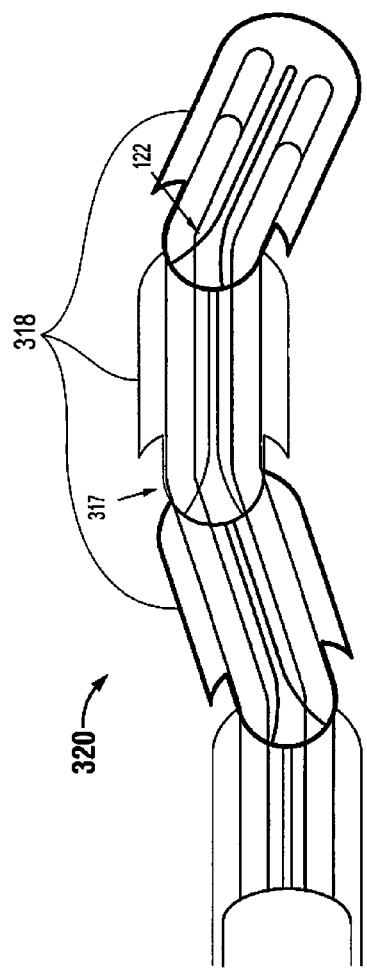
FIG. 8B is a top view of the tool assembly of FIG. 8A illustrating the jaw member formed.
Figure 8C:
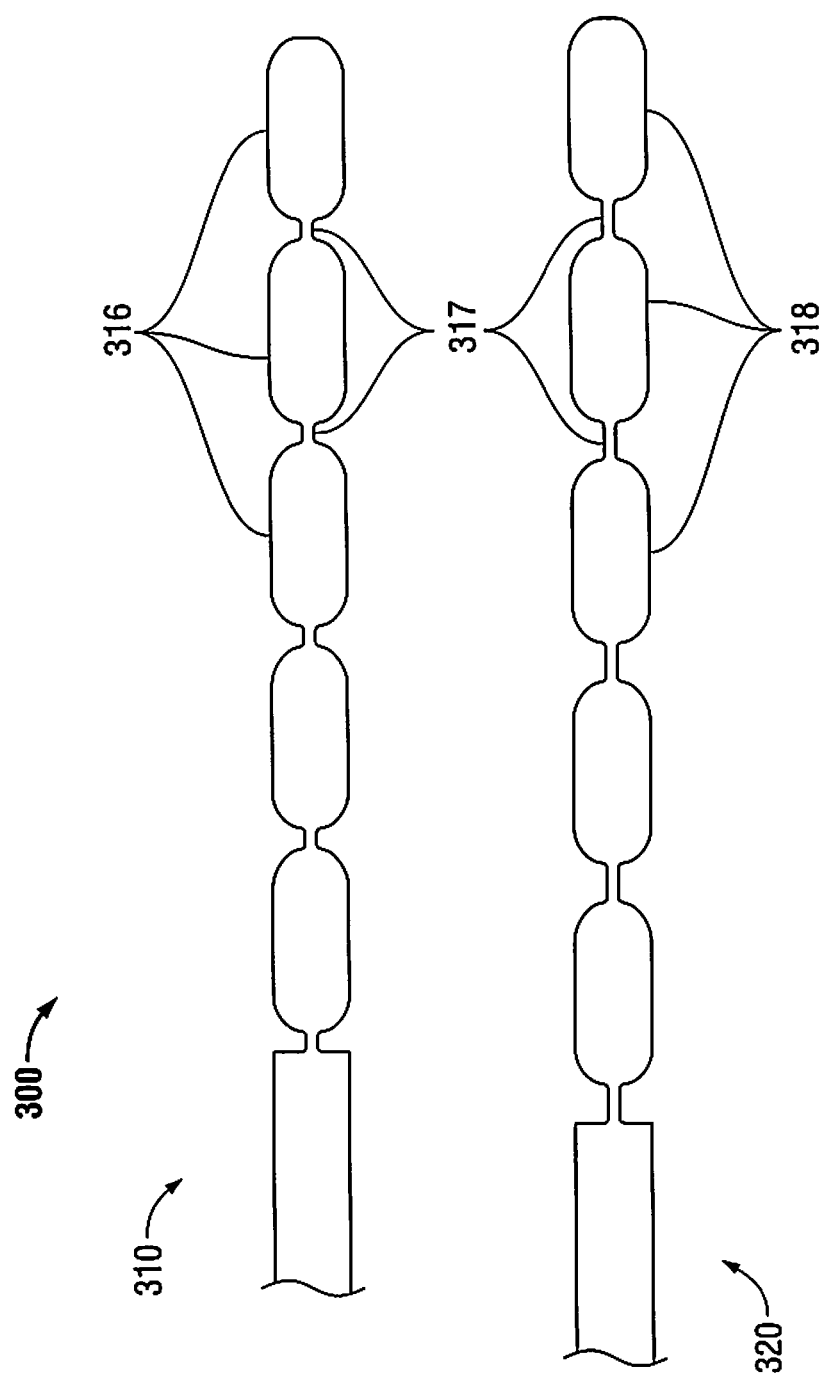
FIG. 8C is a side view of the tool assembly, including the jaw member illustrated in FIGS. 8A and 8B.

In an additional tool assembly embodiment shown in FIGS. 8A, 8B, and 8C, a tool assembly 300 includes a top jaw member 310 and a bottom jaw member 320. Each jaw member 310, 320 includes vertebrae sections 316, 318, respectively, that are each coupled together by a high friction knuckle joint 317. The anvil vertebrae sections 316 of the top jaw member 310 are geometrically mirrored by corresponding vertebrae sections 318 of the stationary bottom jaw member 320. Vertebrae sections 316, 318 may be formed to allow curvature or shape within the range of the knuckle joint 317 (see FIG. 8B) and are held in place by the inherent friction of knuckle joint 317. The semicircular radial channels within the face of each jaw members 310, 320 are defined by radial grooves and an open, semicircular shaped, continuous, memory alloy conduit such as Nitinol. When the vertebrae sections 316, 318 are articulated within each knuckle 317, each continuous shaped memory alloy conduit is allowed to slide or translate distally and/or proximally within their grooves on the distal end of each jaw member 310, 320 to account for the bending deformation within each conduit channel. Knife channels disposed through the jaw members 310, 320 incorporate a convex lead-in geometry which allows the cutting element 122 to find the adjoining slot across each knuckle 317 for each corresponding vertebrae section 316, 318.

In use, the device 10 uses two firing rods 134a, 134b to coincidentally deploy load coils 150 from coil cartridges 148 on opposing sides of cutting element 122. In embodiments, firing rods 134a, 134b may be coupled with the cutting element 122 to advance load coils 150 and cutting element 122 through tissue substantially simultaneously. Alternatively, cutting element 122 and firing rods 134a, 134b may operate independently from each other. In this scenario, tissue may be joined or sealed first, before cutting the joined or sealed tissue via advancement of cutting element 122 therethrough. In other embodiments, the device 10 may be devoid of a cutting element. In other embodiments, two or more load coils 150 may be deployed from each of a plurality of semicircular channels (not shown) on the same plane and on either side of the cutting element 122.

Another embodiment incorporates helically broached grooves defined in the opposing semicircular channels 116, 126 to further captivate each load coil 150 and to enhance tissue anchoring of each load coil 150. The grooves within channels 116, 126 may be used to coil straight or linear wire fasteners (not shown) when advanced therethrough. In this scenario, straight wire fasteners may be utilized in a multi-firing configuration by stacking the straight wire fasteners into a single-fastener width, spring-loaded magazine. The distal ends of firing rods 134a, 134b, in this scenario, may be flat or concave such that distal movement of firing rods 134a, 134b advances the straight wire fasteners into and through the grooves within channels 116, 126 independently.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical fastening device comprising:
   a handle assembly having a stationary handle and a movable handle;
   an elongated member extending distally from the handle assembly, the elongated member including a distal end portion and defining a longitudinal axis extending the length of the elongated member, the elongated member including a pair of stationary coils;
   a pair of firing rods operably coupled with the movable handle and movable between a proximal position and a distal position; and
   a tool assembly mounted to the distal end portion of the elongated member and having a plurality of helical fasteners supported therein, each helical fastener formed of a wire segment having a bend radius, the tool assembly including a pair of opposing jaw members each having at least a pair of semicircular channels disposed therethrough, at least one of the jaw members being movable in relation to the other jaw member between spaced and approximated positions, wherein the semicircular channels of each jaw member are configured to substantially align with the semicircular channels of the other jaw member to form a pair of radial channels when the jaw members are in the approximated position, each of the firing rods configured to advance at least one helical fastener through at least one radial channel and into tissue upon approximation of the movable handle;
   wherein each one of the pair of stationary coils is configured to engage and guide the at least one helical fastener through the elongated member and into the tool assembly.

2. The surgical fastening device according to claim 1, further comprising:
   a cutting element disposed between the pair of radial channels and configured to translate through tissue automatically upon ejection of the at least one helical fastener into tissue.

3. The surgical fastening device of claim 1, wherein the elongated member includes an outer tube that engages the outer surface of the pair of opposing jaw members and biases the pair of opposing jaw members towards the approximated position.

4. The surgical fastening device of claim 2, wherein the cutting element translates when the pair of opposing jaw members are in the approximated position.

5. The surgical fastening device of claim 2, wherein the cutting element is disposed within a frame having the profile of an I-beam.

6. The surgical fastening device of claim 1, wherein the tool assembly includes a biasing member that biases the pair of opposing jaw members towards the spaced position.

7. The surgical fastening device of claim 6, wherein the biasing member is a leaf spring.

8. The surgical fastening device of claim 1, wherein the bend radius is substantially uniform.

9. The surgical fastening device of claim 1, wherein the bend radius is variable.

10. The surgical fastening device of claim 1, wherein each one of the pair of stationary coils is configured to interengage the at least one helical fastener such that a portion of the at least one helical fastener is disposed between two potions of at least one of the pair of stationary coils.

11. The surgical fastening device of claim 10, wherein each one of the pair of stationary coils defines a pitch that is substantially similar to a pitch defined by the at least one helical fastener.

12. A surgical fastening device comprising:
a handle assembly;
an elongated member extending distally from the handle assembly;
a pair of firing rods operably coupled with the handle assembly and being movable between a proximal position and a distal position, each one of the pair of firing rods having a distal portion defining a notch and a chamfer distal of the notch; and
a tool assembly mounted to a distal end portion of the elongated member and having a plurality of helical fasteners supported therein, the tool assembly including a pair of opposing jaw members, at least one of the jaw members being movable in relation to the other jaw member between spaced and approximated positions, wherein in the approximated position, the pair of opposing jaw members together define a pair of radial channels;
wherein the notch on each of the firing rods is configured to engage a tab defined on at least one helical fastener to advance the at least one helical fastener through one of the radial channels and into tissue upon actuation of the handle assembly, and
wherein the at least one helical fastener is configured to slidably engage the chamfer, and the least one helical fastener is configured for radially outward displacement relative to the respective firing rod upon slidable engagement with the chamfer.

13. The surgical fastening device of claim 12, wherein the handle assembly includes a stationary handle and a movable handle.

14. The surgical fastening device of claim 12, wherein the elongated member includes a pair of stationary coils, each of the pair of stationary coils configured to engage the at least one helical fastener.

15. A surgical fastening device comprising:
a handle assembly;
an elongated member extending distally from the handle assembly and including a pair of stationary coils;
a pair of firing rods operably coupled with the handle assembly and being movable between a proximal position and a distal position, each one of the pair of firing rods having a distal portion defining a notch; and
a tool assembly mounted to a distal end portion of the elongated member and having a plurality of helical fasteners supported therein, the tool assembly including a pair of opposing jaw members, at least one of the jaw members being movable in relation to the other jaw member between spaced and approximated positions, wherein in the approximated position, the pair of opposing jaw members together define a pair of radial channels;
wherein the notch on each of the firing rods is configured to engage a tab defined on at least one helical fastener to advance the at least one helical fastener through one of the radial channels and into tissue upon actuation of the handle assembly, and each of the pair of stationary coils is configured to engage the at least one helical fastener.

16. The surgical fastening device of claim 15, wherein the distal portion of each of the firing rods defines a chamfer distally of the notch.

17. The surgical fastening device of claim 16, wherein the at least one helical fastener is configured to slidably engage the chamfer.

18. The surgical fastening device of claim 15, wherein the handle assembly includes a stationary handle and a movable handle.

* * * * *